United States Patent [19]
Frick et al.

[11] 4,371,417
[45] Feb. 1, 1983

[54] DIFFERENTIALLY STRETCHED ELASTIC

[75] Inventors: Richard H. Frick, Neenah; Randolph J. Hill, Appleton; David R. Roland, Winneconne, all of Wis.

[73] Assignee: Kimberly-Clark Corporation, Neenah, Wis.

[21] Appl. No.: 307,423

[22] Filed: Oct. 1, 1981

[51] Int. Cl.³ ............................................. B32B 31/08
[52] U.S. Cl. .............................. 156/495; 112/121.26; 156/164; 156/229; 156/324; 156/554
[58] Field of Search ............... 156/164, 229, 303, 324, 156/495, 554; 112/121.26

[56] References Cited
U.S. PATENT DOCUMENTS

| | | | |
|---|---|---|---|
| 2,670,702 | 3/1954 | Galkin | 112/121.26 |
| 2,681,019 | 6/1954 | Liebowitz et al. | 112/121.26 |
| 2,681,020 | 6/1954 | Leibowitz et al. | 112/121.26 |
| 3,329,549 | 7/1967 | Vilutis | 156/495 |
| 3,443,532 | 5/1969 | Posey et al. | 112/121.26 |
| 4,081,301 | 3/1978 | Buell | 156/495 |
| 4,293,367 | 10/1981 | Klasek et al. | 156/164 |

*Primary Examiner*—Jerome W. Massie
*Attorney, Agent, or Firm*—Leydig, Voit, Osann, Mayer & Holt, Ltd.

[57] ABSTRACT

Apparatus for inserting elastic strips into elastic leg diapers wherein elastic strips are adhesively secured continuously along the crotch area and in relaxed condition along the waist areas including a mechanism for feeding a continuous strip of elastic at a constant rate, a mechanism for feeding a continuous sheet of diaper material at a constant rate, and an oscillating arm for guiding the sheet of diaper material and inducing periodic variations in the velocity or distance of the diaper material with respect to the elastic feeding mechanism, thereby alternately stretching and relaxing predetermined lengths of continuous elastic strips as they are adhesively secured to the diaper material.

9 Claims, 4 Drawing Figures

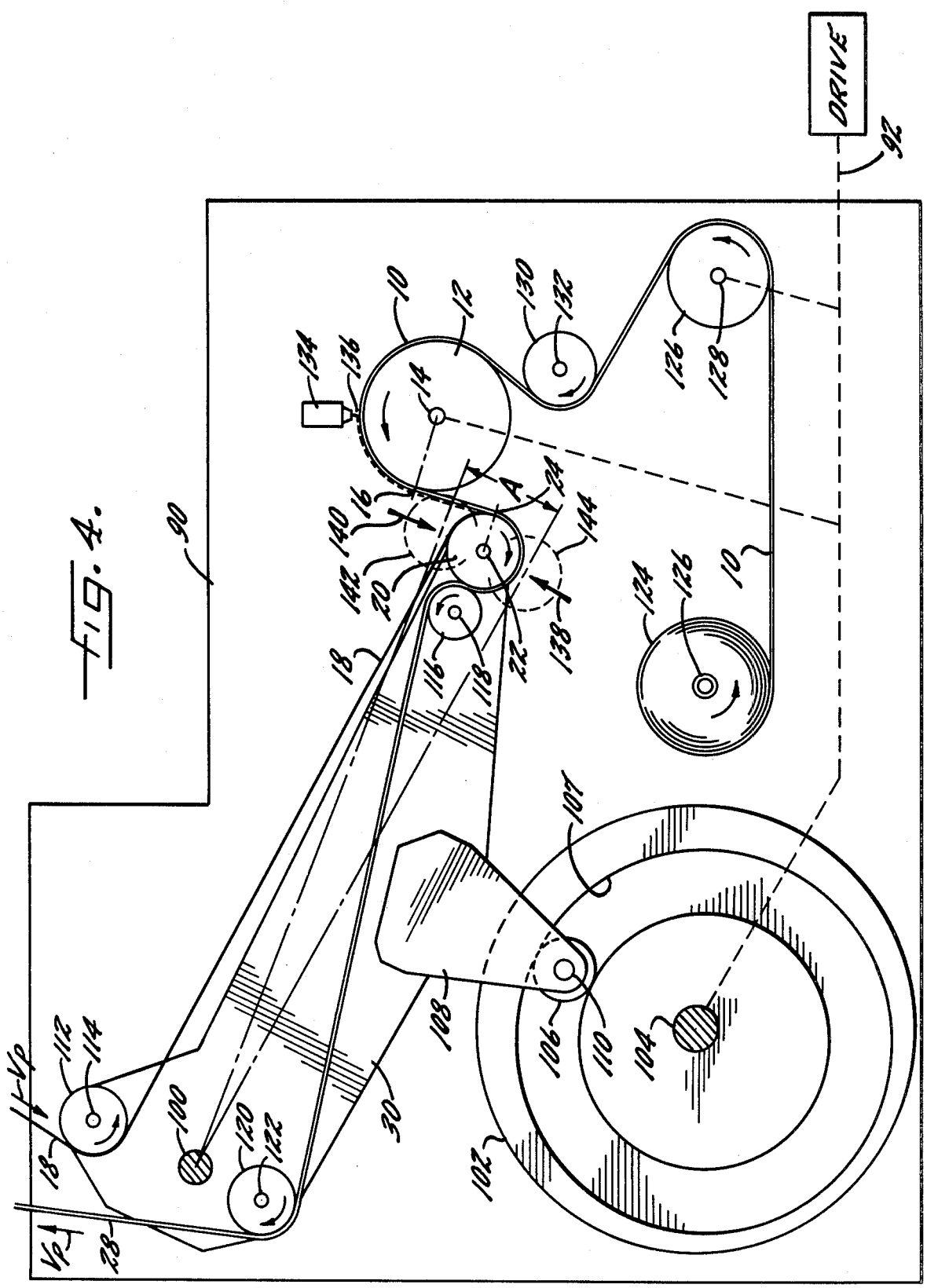

DIFFERENTIALLY STRETCHED ELASTIC

FIELD OF THE INVENTION

This invention relates to an apparatus for applying continuous elastic strips to elastic leg disposable diapers. The elastic strips are adhesively secured continuously along the longitudinal edges of the disposable diaper and are alternately secured in stretched condition along the crotch area and in relaxed condition along the outer waist areas to form gathered and extendible side portions in the crotch area for elastic conformance with the legs of the wearer.

DESCRIPTION OF THE PRIOR ART

(PRIOR ART STATEMENT UNDER RULE 97)

The invention relates generally to the problem of applying a continuous elastic strip alternately secured in stretched and relaxed conditions to a continuous strip or sheet of flexible but substantially non-stretchable material. Liebowitz, U.S. Pat. Nos. 2,681,019 and 2,681,020 both issued June 15, 1954, disclose sewing an elastic strip to a flexible compression-resistant substantially non-stretchable tape in order to put a variable compressive force on the tape to prevent curl in collars and girdles. The elastic strip is placed in alternating degrees of stretch before sewing to the non-elastic tape by tension forces arising between the point of sewing contact and the point at which the elastic strip is tangent to and slips off a stretching roller. Thus the tensile force appeared as a torque on the stretching roller, and is disclosed as a function of the rate at which the elastic strip is fed from the stretching roller and the distance that the elastic strip must travel from the stretching roller to the point of sewing contact.

According to the Liebowitz patents, the rate at which the elastic strip is sewn to the non-elastic tape is essentially constant, since the sewing feed rate of the non-elastic tape is essentially constant throughout the machine in comparison to the rate at which alternations of stretch are impressed upon the elastic strip. In U.S. Pat. No. 2,681,020 the distance that the elastic strip travels from the stretching roller to the point of sewing contact is fixed, and the rate of feed from the stretching roller is alternating, in proportion to the rate of angular rotation of the stretching roller. The stretching roller is driven by the tensile force induced in the elastic tape by the sewing feed and is intermittently permitted to rotate an escapement mechanism attached to the stretching roller and synchronized to the sewing feed.

In U.S. Pat. No. 2,681,019 the distance that the elastic strip travels from the stretching roller to the point of sewing contact is varied along with the angular rate of rotation and tangent velocity at the point at which the elastic strip slips offs the stretching roller, to obtain alternating stretch in the elastic strip as it is sewn to the non-elastic tape. This variation is obtained by employing an eccentrically mounted circular stretching roller, or by using a stretching roller with some other variation in the distance from the roller axis to the periphery of the roller, such as an elliptical variation. Thus a variation in the angular rate of rotation and tangent velocity at the point at which the elastic strip slips off the stretching roller produces a periodic variation even though the drive shaft of the stretching roller is permitted to rotate at a fixed rate, in synchronism with the sewing feed. As a consequence of the means for obtaining a variation in the tangent velocity of the elastic strip as it slips off the stretching roller, the distance from the tangent point to the sewing point also is varied. Liebowitz also appreciated, however, that the variation of the tangential velocity of the stretching roller, setting the elastic feed rate, and the variation of the distance from the tangent point to the sewing point, defining a path length, are independent contributions toward varying the tension in the elastic strip, and thus a variable tension may be obtained with a constant feed rate by cyclically interposing an idler pulley into the path of the elastic strip, thereby varying the path length.

Gore, U.S. Pat. No. 4,239,578 issued Dec. 16, 1980, discloses applying a continuous elastic strip with alternating tension to the longitudinal edges of disposable diapers. Gore varies the tension in the elastic strip by varying the drive shaft angular velocity to the stretching roller, and thus achieves a constant path length from the stretching roller to the point of adhesion of the elastic strips to the disposable diapers. Pneumatic clutches are employed to switch the angular velocity of the stretching roller drive shaft between two different values. An adhesive applicator drum, which spreads adhesive onto the elastic strips and feeds them to the stretching roller, is also geared to the stretching roller. Thus the response of the stretching roller to the clutch engagement is limited by the inertia of the stretching roller and the adhesive applicator. Moreover, the maximum and minimum velocities reached by the stretching roller occur after the period during which the change in stretch is induced in the elastic strip.

Teed, U.S. Pat. No. 4,261,782 issued Apr. 14, 1981, further discloses the method of alternately stretching and relaxing the elastic by periodically interposing an idler pulley into the path of the elastic in a diaper making machine. The displacement of the idler pulley varies the distance of travel of the elastic from a nip and stretching roller. The idler pulley is slowly displaced in a sinusoidal fashion by a crank shaft and is also quickly displaced intermittently by a piston and cylinder driven by compressed air.

SUMMARY OF THE INVENTION

The general aim of the present invention is to provide an apparatus for attaching continuous elastic strips with alternating stretched and relaxed condition to disposable diapers thereby creating gathered and extensivble side protions in the crotch area for elastic conformance with the legs of the diaper wearer.

Moreover, it is an object of the invention to provide an apparatus for application of elastic strips wherein the diaper material is fed into and out of the elastic strip adhesion apparatus at a constant rate, and the elastic strips are also fed into the apparatus at a constant rate and receive adhesive at a constant rate.

Furthermore, it is an object of the invention to provide means for imparting alternating stretch to the elastic strips by varying the tangential receiving rate at the bonding point.

It is also an object of the invention to vary the difference in tangential elastic feeding and receiving rate by reciprocating rectilinear motion via a cam mechanism in order to eliminate friction clutches.

Yet another object of the invention is to provide a cam profile which imparts a maximum and minimum tangenial receiving rate at the times during which the change in stretch is induced in the elastic strip, thereby maximizing the gradient of stretch of the elastic strip after it is bonded to the disposable diaper.

The present invention involves the elastic adhesion step in the manufacture of disposable diapers typically composed of a highly absorbent material sandwiched between a fluid permeable facing sheet and a fluid impervious poly backing sheet.

In accordance with the present invention, the disposable diaper poly backing is fed around a pivoted, oscillator frame which is driven by a cam via a cam follower secured to the oscillator frame. The poly backing is fed in and out of the oscillator frame by two feed rollers that are closely spaced from the pivot shaft along a line perpendicular to the oscillator frame radius, so that the poly feed rate is substantially constant in and out of the feed rollers as the poly is fed generally perpendicular to the oscillator frame radius. The poly travels radially from the pivot area to the bonding point at the end of the oscillator frame. The tangential velocity of the poly around the end of the oscillator frame is then the constant feed velocity plus or minus the tangential velocity of the pivot arm, as determined by the cam profile.

A continuous elastic strip is fed at a constant rate over a stretching roller driven at a constant angular velocity, and adhesive is applied to the elastic strip. The stretching roller is fixed, closely positioned and generally tangent to the arc swung by the end of the pivoting oscillator frame, so that the adhesive backed elastic strip slips off the stretching roller and bonds to the poly as the poly moves tangent to the stretching roller. The stretch in the bonded elastic strip is then proportional to the difference between the tangential velocity of the stretching roller and the tangential velocity of the poly, so that alternations in stretch are induced by the variations in tangential velocity set by the cam profile.

Optionally the cam profile has an enhanced velocity at the beginning of the changes in stretch, and the end of the oscillator frame is arc shaped and in continuous contact with the stretching roller, so that the change in velocity is quickly transferred to a change in the stretch of the bonded elastic strip. Satisfactory results, however, have been obtained with a simple roller on the end of the oscillator frame and a cam profile generating a velocity that alternates between two constant values.

DESCRIPTION OF THE PREFERRED EMBODIMENT

The present invention pertains to part of a machine for continuously assembling elastic leg disposable diapers. The machine sandwiches a highly absorbent material between a fluid permeable facing sheet and a fluid impervious poly backing sheet. The specific construction of the disposable diaper is the subject of a copending application titled "Disposable Diaper With Elasticised Leg Openings" by W. Sigl and R. Frick and assigned to the assignee of the present invention, but the present invention is equally applicable to other disposable diaper designs, including the design disclosed by Gore, U.S. Pat. No. 4,239,578 issued Dec. 16, 1980. The present invention involves the part of the diaper assembly machine that bonds elastic strips to the diaper material for elasticizing the leg openings of the finished diapers.

Figure 1:
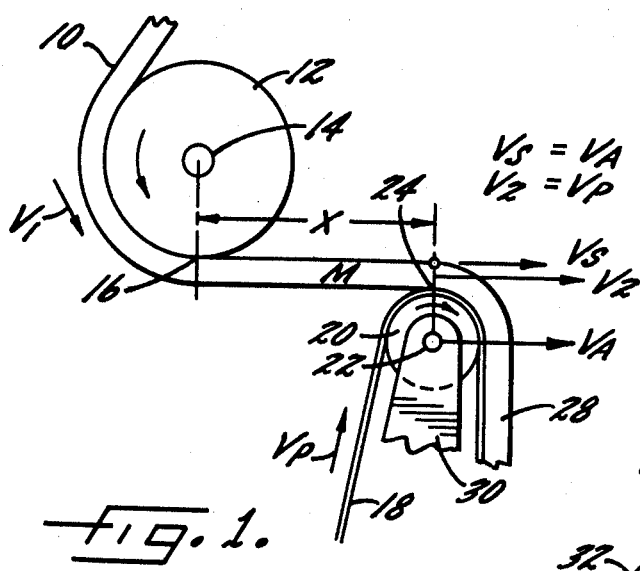
FIG. 1 is a schematic illustration of the preferred embodiment of the invention, including the relevant mathematical parameters which define its operation.

Turning now to the drawings, FIG. 1 schematically shows the mechanism whereby differential stretch is imparted to an elastic strip 10 as it is bonded to poly backing sheet 18. The continuous elastic strip 10 is fed at a generally constant rate $V_1$ by a fixed stretching roller 12 rotated by shaft 14. The elastic strip slips off the stretching roller 12 at the tangent point 16 and is picked up by oscillator roller 20. Oscillator roller 20 is journaled for free rotation about shaft 22 secured to a movable oscillator frame 30. A continuous sheet of poly backing material 18 is also fed around oscillator roller 20, and receives the elastic at a tangent point 24. The poly with adhered elastic 28 is then pulled off the oscillator roller 20 for further processing in a diaper assembly line.

Differential stretch is induced in the elastic strip 10 as it travels over distance X between the tangent points 16 and 24. The stretch S of the elastic 10 may be defined in terms of the linear density dX/dM of the elastic 10. With the units of the mass, M, chosen so that the linear density dX/dM of the unstretched elastic 10 is equal to 1, the elongation E is directly proportional to linear density:

$$E = dX/dM = X/M \tag{1}$$

where M is the total mass of the elastic strip 10 between the tangent points 16 and 24. Since the process whereby the elastic 10 is carried or taken up by the rollers 12, 20 is a form of gear engagement, the elongation of the elastic 10 as it is bonded to the poly backing 18 is the same as the elongation of elastic strip 10 between the tangent points.

The stretch S may also be defined in terms of the elongation E as:

$$S = E - 1 \tag{2}$$

The velocity $V_1$ of the elastic 10 as it travels around the stretching roller 12 is porportional to the radius and angular velocity of the stretching roller 12. Similarly the velocity $V_P$ of the poly backing 18 fed to the oscillator roller 20 is proportional to the radius and the angular velocity of the oscillator roller 20. The rate at which the elastic 10 between the tangent points 16, 24 is taken up by the oscillator roller 20 is defined as $V_2$, which is FIG. 1 equals $V_p$.

$V_1$ and $V_2$ are functionally related to the elongation E and stretch S via the mass M of the elastic 10 by the conservation of mass equation:

$$dM/dt = dM/dt \text{ in } + dM/dt \text{ out}$$
$$= V_1 - (M/X)V_2 = V_1 - (V_2/E) \tag{3}$$

In general, X is not independent of time, and is related to the velocity $V_s$ of the tangent point 24 of the oscillator roller 22 with respect to the tangent point 16 of the stretching roller 12:

$$V_s = dX/dt \tag{4}$$

In FIG. 1 $V_s = V_a$, the tangential velocity of the oscillator frame 30.

Equations (1) through (4) supra completely define the stretch of the elastic strip bonded to the poly 28. The general solution, however, is non-linear. The solution for $dE/dt = 0$ is of interest since then $dX/dt = EdM/dt$ and therefore:

$$\text{for } dE/dt = 0, \; V_s = EV_1 = V_2 \tag{5}$$

or equivalently for FIG. 1, $V_A = EV_1 - V_p$. By setting $V_p = 1.5V_1$, for example, $V_A = -0.5\, V_1$ for $E = 1$ and $V_a = +0.5\, V_1$ for $E = 2$.

The solution for $V_s = 0$ is also of interest since then equation (3) is linear and has the solutions:

$$\text{For } V_s = 0, \; M = \left( M_o - \frac{V_1 X}{V_2} \right) e^{-\frac{V_2 t}{X}} + \frac{V_1 X}{V_2} \tag{6}$$

$$\text{For } V_s = 0, \; E = \left( \left( \frac{1}{E_o} - \frac{V_1}{V_2} \right) e^{-\frac{V_2 t}{X}} + \frac{V_1}{V_2} \right)^{-1} \tag{7}$$

Figure 3:
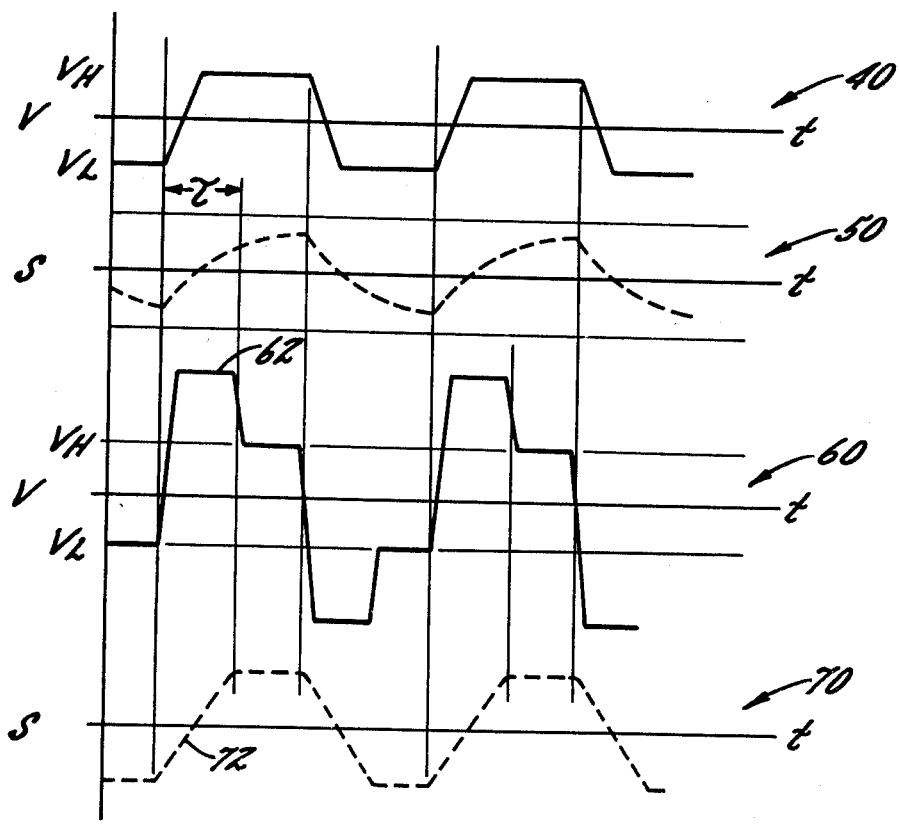
FIG. 3 is an illustration of induced stretch as a function of velocity variations; and, FIG. 4 is a detailed diagrammatic illustration of the invention as employed in a diaper assembly line.

Thus a time constant $\tau = X/V_2$ defines the response of the elongation to changes in $V_2$ or $V_1$. As shown in FIG. 3, if a velocity $V$ which may be either $V_1$, $V_2$, or $V_p$ is switched between two values $V_L$ and $V_H$ as illustrated by the trapezoidal waveform generally designated 40, the response of the stretch S as illustrated by the waveform generally designated 50 has a triangular shape caused by a time delay measured by the time constant $\tau$.

Figure 2:
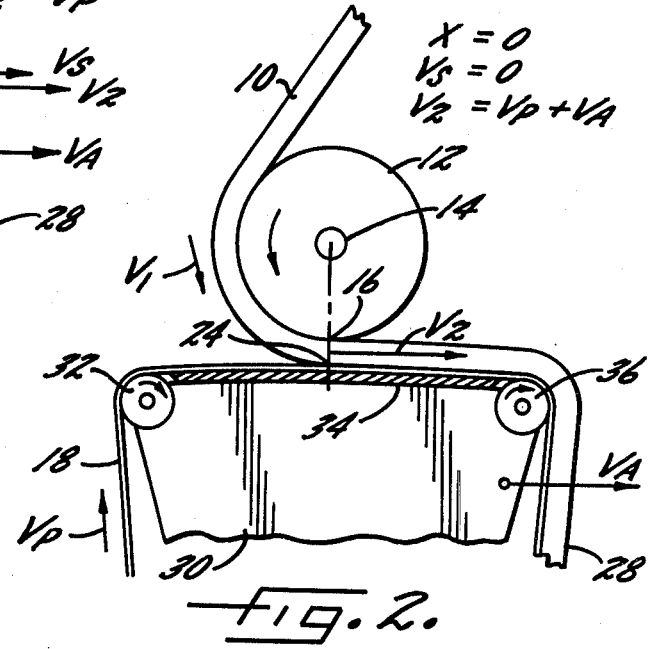
FIG. 2 is a schematic illustration of an alternate embodiment of the invention which, with greater precision, provides transfer of the elastic strips from the stretching roller directly to the poly backing.

In practice a stretch S that rapidly changes from a stretched to an unstretched condition is desirable. One method to obtain a rapid change is to reduce the time constant $\tau$ by decreasing the distance X. As shown in FIG. 2, the tangent point 16 of the elastic strip 10 with the stretching roller 12 may be made coincident with the tangent of contact 24 with the poly backing 18 by providing the oscillator frame 30 with an arcuate face plate 34 to press the poly backing in contact with the elastic 10 as the elastic slips off the stretching roller 12. Rollers 32 and 36 are provided at the ends of the face plate 34 and journaled to the oscillator frame 30 for free rotation to reduce the sliding friction of the poly backing 18 around the ends of the face plate 34. The geometry in FIG. 2 indicates that the velocity $V_2$ at which the elastic 10 is taken up by the poly 18 is the sum of the poly velocity $V_p$ and the tangential velocity $V_A$ of the oscillator frame 30.

The geometry in FIG. 2 is more complicated than the geometry in FIG. 1 and thus it is desirable to find another way to reduce the delay in the response of the stretch S to changes in velocity V. Although the time constant $\tau$ is inversely proportional to $V_2$, increasing $V_2$ does not help since the distance on the final diaper product over which the stretch is changing is the result to be minimized and this distance is defined by X and is independent of $V_2$. The response of slew rate of the stretch S may, however, be increased by peaking either $V_1$ or $V_S$ while the stretch S is changing, as shown by the waveforms generally designated 60 and 70 in FIG. 3. The peaking 62 may be adjusted to obtain a desired rate of slew 72. Peaking of $V_S$ is easily obtained by varying the tangential velocity $V_A$ of the oscillator frame 30.

Pursuant to the present invention and as shown in FIG. 4, variations in the tangential velocity $V_A$ are generated by the profile of an eccentric cam 102. A recessed track 107 in the cam 102 is provided to receive a cam follower 106 journaled via pin 110 to bracket 108 fastened to the oscillator frame 30. The oscillator frame 30 pivots about a shaft 100 affixed to the frame 90 of the diaper making machine. As cam 102 is rotated by a drive shaft 104 of the machine drive 92, the oscillator frame 30 is tangentially displaced periodically in an upward direction 138 and downward direction 140 through a displacement A. The maximum upward displacement 142 and downward displacement 144 are indicated by phantom lines.

In the preferred embodiment, rollers 112 and 120 are journaled to the oscillator frame 30 by shafts 114 and 122 and are positioned about the pivot 100 along a line perpendicular to the longitudinal axis of the oscillator frame, thereby minimizing variations in the feed rate $V_P$ caused by variations in the tangential velocity $V_A$ of the oscillator frame 30.

The elastic 10 is obtained from a spool 124 which may freely rotate around shaft 126 affixed to the machine frame 90 as the elastic is pulled by a preheat roll 126 driven by a drive shaft 128 of the machine drive 92. The elastic 10 passes around idler 130 journaled to shaft 132 affixed to the machine frame 90. The elastic then passes around a stretching chill roller 12 driven by a drive shaft 14 of the machine drive 92, and glue from a glue gun 134 is applied to the elastic 10 at point 136. The elastic 10 slips off the stretching chill roller 12 at tangent point 16.

The elastic 10 and poly backing 18 are then both fed to the oscillator roller 20 which is journaled on shaft 22 fixed to the oscillator frame 30. The elastic 10, having differential stretch induced by displacement of the oscillator frame 30, bonds to the poly 18 at the tangent point 24 of the oscillator roller 20 and the poly and bonded elastic 28 are fed around idler roller 116 journaled on shaft 118 fixed to the oscillator frame 30. From idler roller 116 the poly and bonded elastic 28 pass around roller 120 and exit from the elastic bonding portion of the diaper assembly line.

The preferred embodiment of FIG. 4 provides satisfactory differential stretch during the manufacture of diapers even without peaking of the oscillator frame 30 tangential velocity $V_A$. Typically the feed rate of the poly backing $V_P$ is set about 1.5 times the feed rate of the elastic $V_1$ and a triangular displacement cam profile is used to switch the oscillator frame velocity $V_A$ between plus and minus one-half the elastic feed rate $V_1$. Eighteen inch diapers, for example, may be manufactured using an arc displacement A of three inches, an oscillator frame velocity $V_A$ of plus and minus eight feet per minute, an elastic feed rate $V_1$ of sixteen feet per minute, and a poly feed rate $V_P$ of twenty-four feet per minute.

The present disclosure includes that contained in the appended claims, as well as that of the foregoing description. Although this invention has been described in its preferred form with a certain degree of particularity, it is understood that the present disclosure of the preferred form has been made only by way of examples and that numerous changes in details of construction and the combination and arrangement of parts may be resorted to without departing from the spirit and scope of the invention as hereinafter claimed. In FIG. 4, for example, the elastic 10 is bonded to the poly backing 18, but in alternative diaper designs the elastic 10 could be bonded to the fluid permeable facing sheet by replacing the poly 18 with the fluid permeable facing sheet. Moreover, the adhesive could be applied to the poly backing 18 or fluid permeable sheet before bonding to the elastic 10 without substantially affecting the result. These are just a few of the modifications obvious to persons skilled in the art.

What is claimed is:

1. In an apparatus for attaching elastic strips in elastic leg disposable diapers having elasticized leg openings during the manufacture of such diapers moving in serially-interconnected form in an assembly machine and including means for feeding continuous elastic strips into desired positions in the diaper for adhesive attachment continuously along the longitudinal edges of the diapers and means for alternately stretching and relaxing predetermined lengths of the elastic strips during the feeding thereof for attaching the stretched lengths to the crotch area and substantially relaxed lengths to the outer waist areas; the improvement of said means for alternately stretching and relaxing predetermined lengths of the continuous elastic strips comprising:

(a) a movable guiding means for guiding the flow of the serially-interconnected diaper material along a predefined but movable path, and (b) periodic driving means connected to the movable guiding means for periodically displacing the predefined path of the serially-interconnected diaper material with respect to the means for feeding the continuous elastic strips, thereby alternately relaxing and stretching the elastic fed to and bonded to the diaper material.

2. In an apparatus, as defined in claim 1, in which said periodic driving means includes a rotary cam, and said movable guiding means comprises a pivoted oscillator frame periodically subtending an arc when driven by the periodic driving means.

3. In an apparatus, as defined in claim 2, in which said oscillator frame further includes a cylindrical roller means journaled to the moving end of the oscillator frame for guiding the flow of the serially-interconnected diaper material around the moving end of the oscillator frame.

4. In an apparatus, as defined in claim 2, in which said pivoted oscillator frame further includes an arcuate plate, attached to the movable end of the pivoted oscillator frame, cylindrical with respect to the pivot axis, for guiding the flow of the serially-interconnected diaper material around the moving end of the oscillator frame.

5. Apparatus for manufacturing elastic leg disposable diapers having elasticised leg openings, said apparatus including a diaper material feed means providing a continuous stream of diaper material at a generally constant rate and means for applying continuous strips of elastic in alternately stretched and relaxed condition along predetermined length intervals to the continuous stream of diaper material, said means for applying the continuous strips of elastic comprising:

(a) elastic feed means for feeding continuous strips of elastic, in a generally relaxed condition at a controlled rate substantially slower than the feed rate of the diaper material feed means, to the stream of diaper material, and (b) oscillating guiding means for defining and periodically displacing the stream of diaper material in which the periodic displacement of the stream periodically increases and decreases the velocity of the stream of diaper material with respect to the elastic feed means at the point of contact of the elastic strips and the stream of diaper material, thereby periodically extending and relaxing the elastic strips as they are applied to the stream of diaper material.

6. The apparatus as defined in claim 5, wherein said oscillating guiding means includes a pivoted arm having a cam follower engaging a rotary cam, said cam having a profile causing periodic displacement of the cam follower, thereby periodically displacing the stream of diaper material.

7. The apparatus as defined in claim 6, wherein said pivoted arm further includes a cylindrical roller journaled to the moving end of the pivoted arm, thereby providing means for guiding the stream of diaper material around the moving end of the pivoted arm, and periodically varying the tangential velocity of the diaper material, at points on the cylindrical roller opposite from the pivot of the pivoted arm, with respect to the diaper feeding means.

8. The apparatus as defined in claim 6, wherein said pivoted arm further includes an arcuate plate attached to the moving end of the pivoted arm, with an arcuate surface lying on a cylinder having an axis generally collinear with the axis of the pivot of the pivoted arm, thereby providing a surface for guiding the stream of diaper material around the moving end of the pivoted arm, in which periodic displacement of the pivoted arm periodically varies the tangential velocity of the stream of diaper material, and providing a fixed tangent point for receiving elastic strips fed by the elastic feeding means.

9. The apparatus as defined in claim 6, wherein said pivoted arm further includes a diaper material stream receiving roller and a diaper material stream expending roller, said rollers journaled to the pivoted arm near the pivot point, thereby providing a means of receiving the diaper stream, passing the stream to the moving portion of the pivoted arm, and expending the diaper material stream with attached elastic, all at a generally constant rate, generally independent of the pivoting motion of the pivoted arm.

* * * * *

UNITED STATES PATENT AND TRADEMARK OFFICE
CERTIFICATE OF CORRECTION

PATENT NO. : 4,371,417
DATED : February 1, 1983
INVENTOR(S) : Richard H. Frick, Randolph J. Hill and David R. Roland It is certified that error appears in the above—identified patent and that said Letters Patent is hereby corrected as shown below:

Col. 5, line 8, change "for $dE/dt=0$, $Vs=EV_1=V_2$" to

--for $dE/dt=0$, $V_s=EV_1-V_2$--.

Signed and Sealed this

Nineteenth Day of April 1983

[SEAL]

Attest:

GERALD J. MOSSINGHOFF

Attesting Officer

Commissioner of Patents and Trademarks